United States Patent [19]

Grassi et al.

[11] Patent Number: 5,564,923
[45] Date of Patent: Oct. 15, 1996

[54] PROSTHETIC IMPLANT FOR PROSTHODONTICS

[75] Inventors: Luigi Grassi, Magenta; Rodolfo Ferrara, Pieve Emanuele, both of Italy

[73] Assignee: New Line S.r.l., Cornaredo, Italy

[21] Appl. No.: 371,177

[22] Filed: Jan. 11, 1995

[30] Foreign Application Priority Data

Jan. 26, 1994 [IT] Italy ................. MI94A0129

[51] Int. Cl.$^6$ ................... A61C 8/00
[52] U.S. Cl. ................... 433/173
[58] Field of Search ........... 433/172, 173, 433/174, 175, 176, 201.1

[56] References Cited

U.S. PATENT DOCUMENTS

| | | | |
|---|---|---|---|
| 4,960,381 | 10/1990 | Niznick | 433/173 X |
| 5,030,096 | 7/1991 | Hurson et al. | 433/173 |
| 5,135,395 | 8/1992 | Marlin | 433/173 X |
| 5,145,372 | 9/1992 | Daftary et al. | 433/173 |
| 5,195,891 | 3/1993 | Sulc | 433/173 |
| 5,213,500 | 5/1993 | Salazar et al. | 433/173 X |
| 5,312,256 | 5/1994 | Scortecci | 433/173 X |
| 5,316,476 | 5/1994 | Krauser | 433/173 |
| 5,328,371 | 7/1994 | Hund et al. | 433/173 |
| 5,342,199 | 8/1994 | Gillespie | 433/173 |
| 5,344,457 | 9/1994 | Pilliar et al. | 433/174 X |
| 5,433,606 | 7/1995 | Niznick et al. | 433/173 |

Primary Examiner—Nicholas D. Lucchesi
Attorney, Agent, or Firm—Guido Modiano; Albert Josif

[57] ABSTRACT

Prosthetic implant for prosthodontics which comprises an elongated intrabony body made of titanium which is to be substantially fully inserted within a receptacle formed in a mandibular or maxillary bone. The intrabony body has, at its proximal end which is to be located at the surface layer of the mandibular or maxillary bone, engagement means for a stump that supports a false tooth or a prosthesis. The external surface of the intrabony body has a roughness that is adapted to increase its integration with the bone except for a smooth portion which is provided starting from the proximal end.

17 Claims, 3 Drawing Sheets

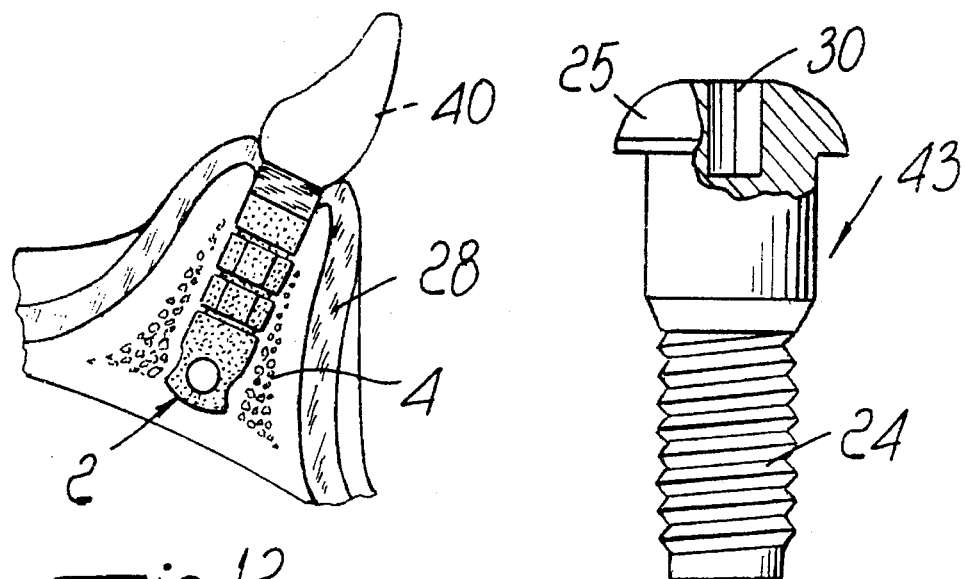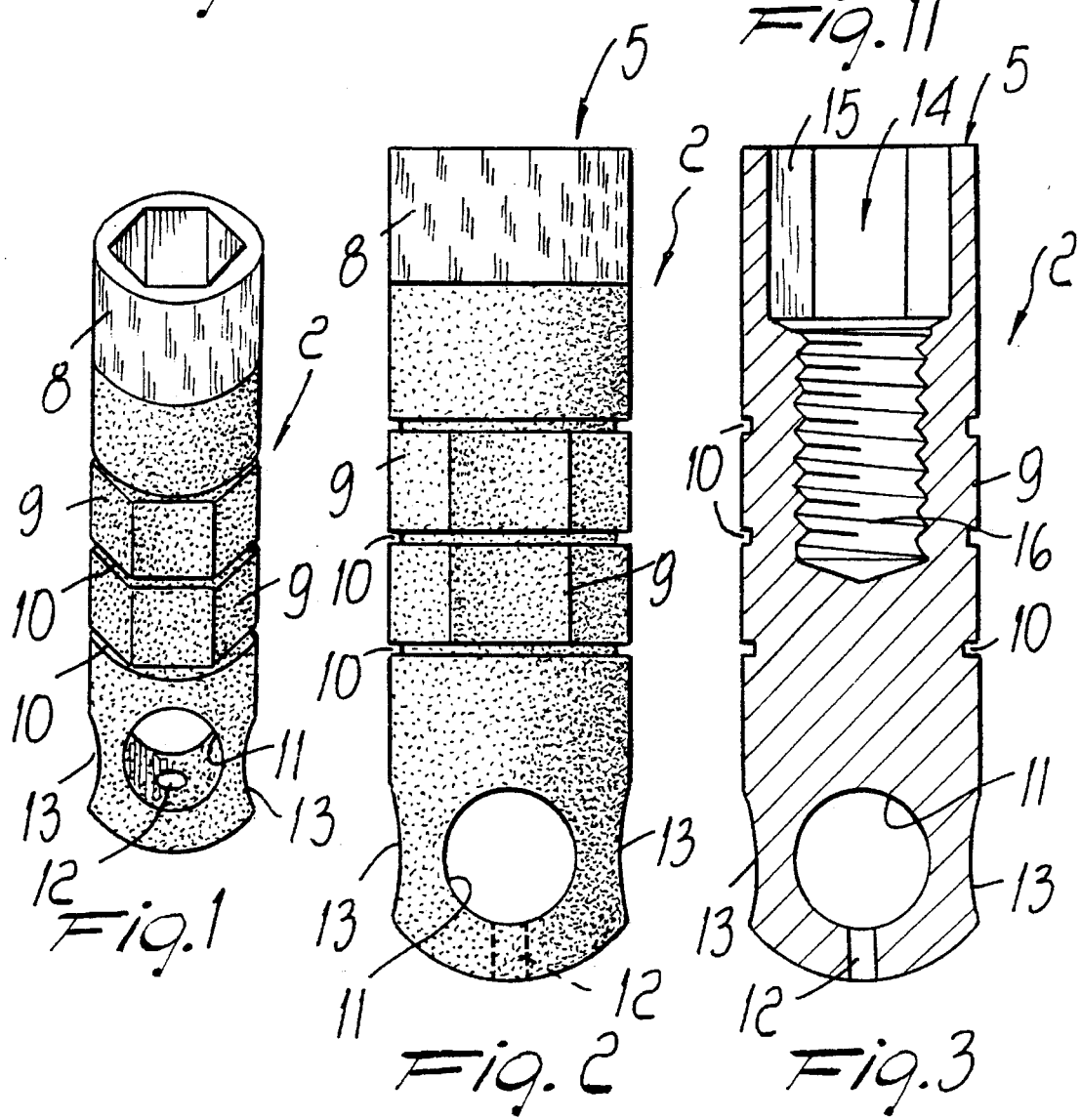

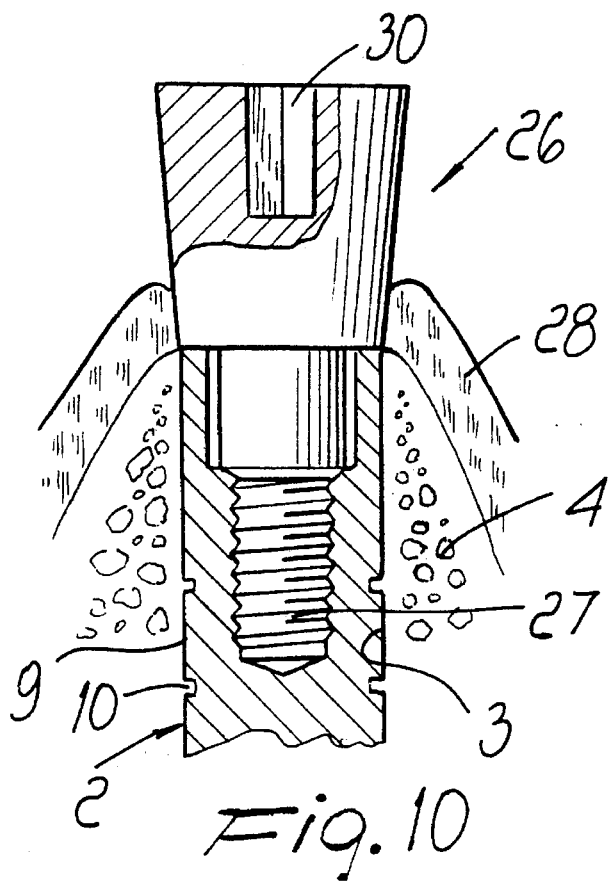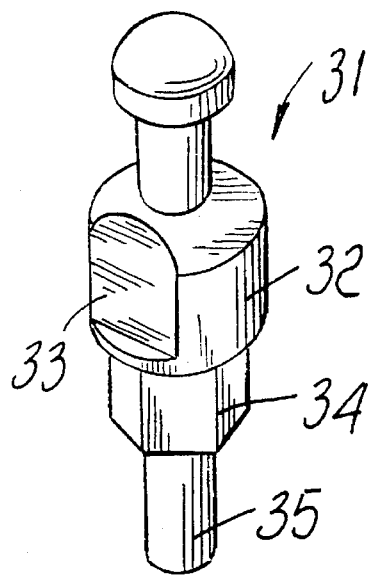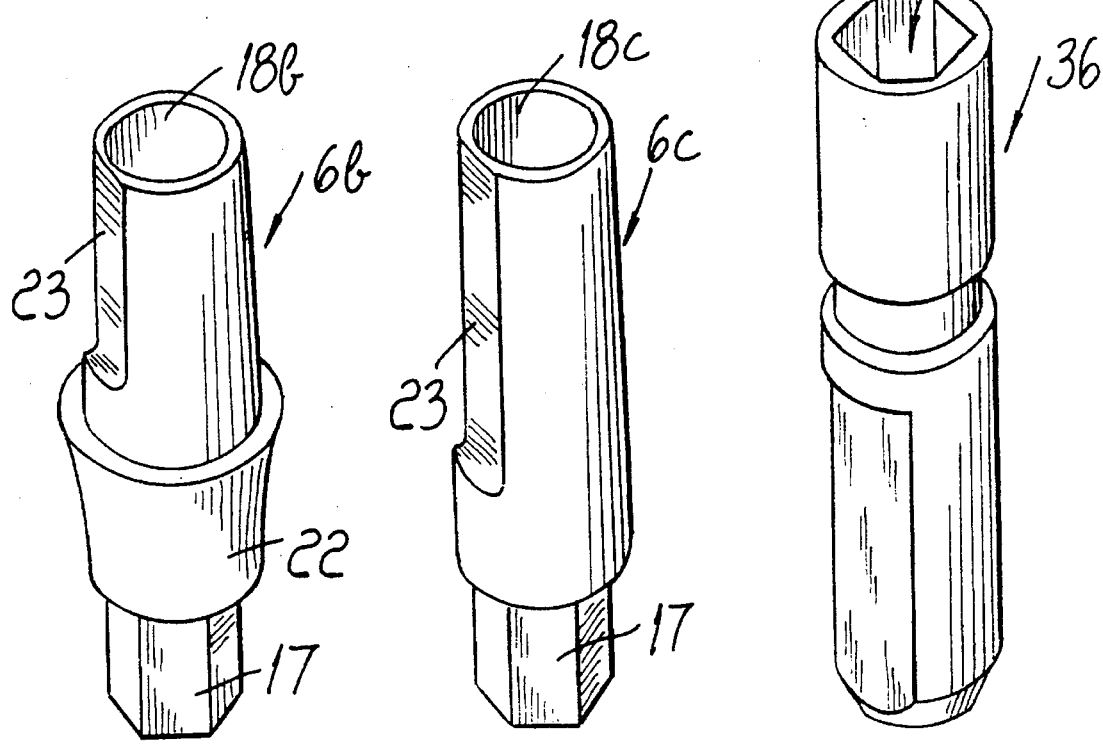

PROSTHETIC IMPLANT FOR PROSTHODONTICS

BACKGROUND OF THE INVENTION

The present invention relates to a prosthetic implant for prosthodontics.

It is known that the various prosthodontic techniques currently being used entail an extensive use of intrabony bodies, that is to say, of bodies which are to be inserted in the mandibular or maxillary bone and are usually made of titanium owing to the property of this metal of being integrated by bone tissue.

Depending on the configuration and types of application, these intrabony bodies are distinguished into screws, plugs, baskets, etc.

In most cases, the intrabony body of the implant is an elongated body which is fully or almost fully inserted in a receptacle which is appropriately provided in the mandibular or maxillary bone and is left therein for a period that varies according to the physiological characteristics of the patient and in any case for a few months before being used as anchoring point for a false tooth or for a more complicated prosthesis.

Adapted pins and stumps are used to anchor the tooth or the prosthesis and are fixed with various techniques to the proximal end of the intrabony body, that is to say, to the end of said body that is located proximate to the surface layer of the bone in which said body is inserted.

In order to facilitate bone integration, the intrabony bodies currently being used have a finely rough surface. This roughness, which is intentionally sought, can cause problems after the prosthodontic operation.

In the first two years after the operation, the bone in fact tends to shrink at the receptacle that accommodates the intrabony body of the implant; this shrinkage partially exposes the intrabony body proximate to its proximal end. The part of the intrabony body abandoned by the bone makes contact with the gingival mucous membrane, often producing inflammations of this tissue which poorly tolerates contact with the rough surface of the intrabony body of the implant.

SUMMARY OF THE INVENTION

The aim of the present invention is to solve the above described problem by providing a prosthetic implant for prosthodontics which can significantly limit irritations of the gingival mucous membrane caused by bone shrinkage at the implant.

Within the scope of this aim, an object of the invention is to provide an implant that offers adequate assurances as regards its integration in the bone.

Another object of the invention is to propose an implant that can be applied with currently used prosthodontic methods.

This aim, these objects, and others which will become apparent hereinafter are achieved by a prosthetic implant for prosthodontics which comprises an elongated intrabony body made of titanium which is to be substantially fully inserted within a receptacle formed in a mandibular or maxillary bone, said intrabony body having, at its proximal end which is to be located at the surface layer of the mandibular or maxillary bone, engagement means for a stump that supports a false tooth or a prosthesis, characterized in that the external surface of said intrabony body has a roughness that is adapted to increase its integration in the bone except for a smooth portion which is provided starting from said proximal end.

BRIEF DESCRIPTION OF THE DRAWINGS

Further characteristics and advantages of the invention will become apparent from the description of a preferred but not exclusive embodiment of the prosthetic implant according to the invention, illustrated only by way of non-limitative example in the accompanying drawings, wherein:

FIG. 1 is a perspective view of the intrabony body of the prosthetic implant;

FIG. 2 is a lateral elevation view of the intrabony body;

FIG. 3 is an axial sectional view of the intrabony body;

FIGS. 6 and 7 are perspective views of two types of stump that can be applied to the intrabony body in the prosthetic implant according to the invention;

FIG. 8 is a perspective view of a transfer stump of the prosthetic implant according to the invention;

FIG. 9 is a perspective view of an element for replacing the intrabony body which is to be embedded in the plaster cast to form dental prostheses;

FIG. 10 is a view of the intrabony body inserted in the bone tissue and with a healing screw applied thereto;

FIG. 11 is a partially sectional lateral elevation view of a plug screw of the prosthetic implant; and FIG. 12 is a view of the implant according to the invention, anchored to the bone tissue, with a false tooth applied there to.

DESCRIPTION OF THE PREFERRED EMBODIMENTS

Figure 5:
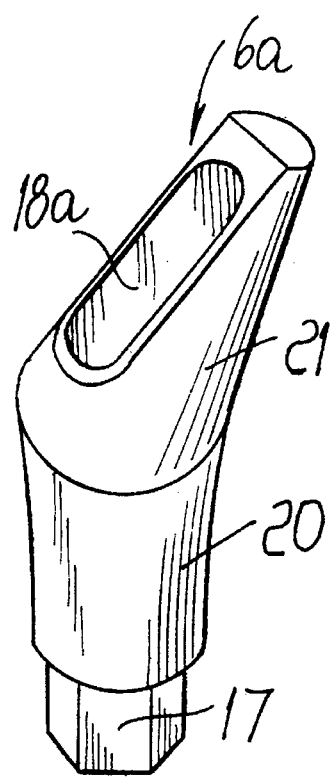
FIG. 5 is a perspective view of the angled stump of FIG. 4.
Figure 4:
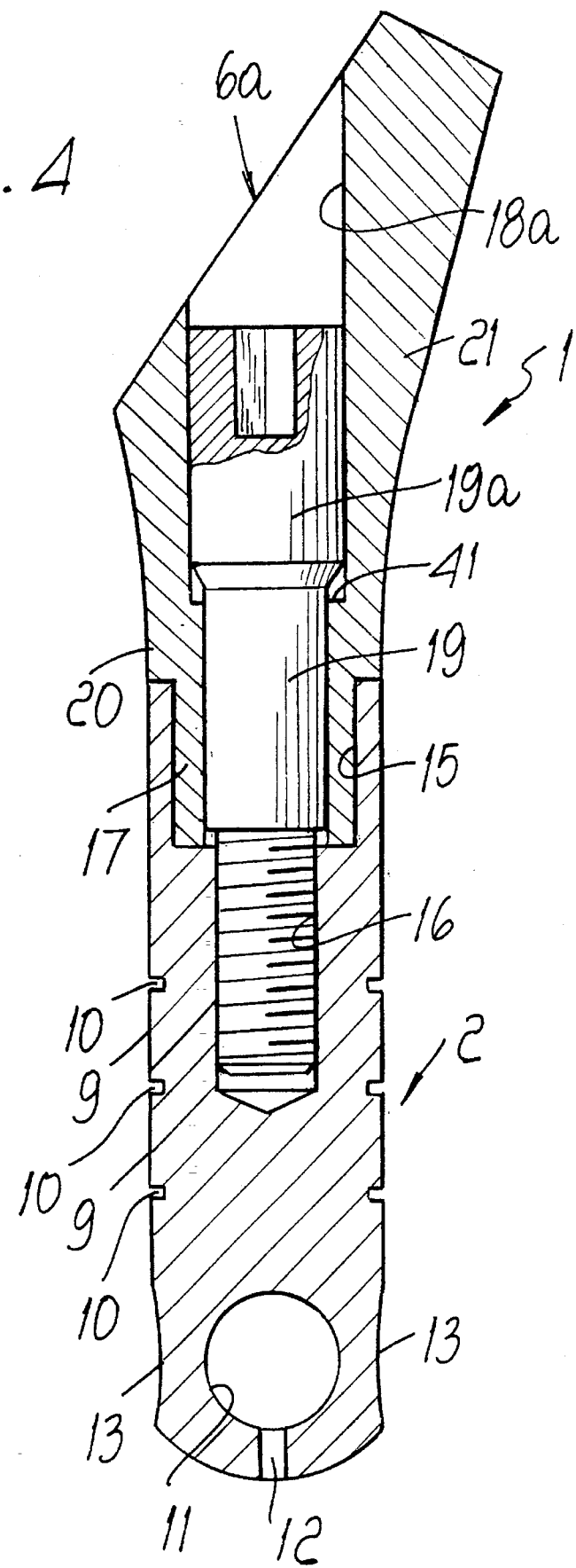
FIG. 4 is an axial sectional view of the prosthetic implant with an angled stump.

With reference to the above figures, the implant according to the invention, generally designated by the reference numeral 1, comprises an intrabony body 2, that is to say, a body which is to be inserted substantially fully within a receptacle formed in a mandibular or maxillary bone 4. The intrabony body 2 has an elongated shape, preferably a substantially cylindrical one, and is made of titanium, so as to offer adequate assurances of integration with the bone. The body 2 has, at its proximal end 5, that is to say at its end meant to be located at the surface layer of the mandibular or maxillary bone, engagement means for a stump 6a, 6b, or 6c on which a false tooth 40 is reconstructed or which is used as anchoring point for a more complex prosthesis.

According to the invention, the intrabony body 2 has an outer surface which has a roughness that is adapted to increase its integration with the bone, with the exception of a smooth portion 8 which is provided starting from the proximal end 5.

Conveniently, at least one intermediate portion 9 of the body 2 has a prism-like shape that is coaxial to the remaining part of the intrabony body 2 such that the intermediate portion has a recitilineal cross-section taken in a plane substantially perpendicular to the longitudinal axis of the intrabony body 2 extending between the distal and proximal ends thereof; in the illustrated case, there are two intermediate portions 9.

The prism-shaped portions 9 are separated from each other and from the remaining part of the body 2 by circumferential grooves 10. As seen in the FIGS. 1–3, the grooves 10 have diameters which are less than the maximum diameters of the outer surfaces of the prism-shaped intermediate portions 9 and of the remaining cylindrical upper and lower portions of the body 2. Said grooves 10 have the purpose of axially locking the body 2 in the bone tissue, once integration with the bone has been achieved, whereas the prism-shaped portions 9 rotationally lock the body 2.

The body 2 is crossed, proximate to its distal end, by a transverse hole 11 which also has the purpose of stably anchoring the body 2 in the bone tissue following integration with the bone.

The body 2 also has, again at its distal end, an axial hole 12 that leads into the transverse hole 11.

Recesses 13 are formed on the outer surface of the body 2 proximate to its distal end and are angularly spaced from the transverse hole 11 about the longitudinal axis of the body 2.

The engagement means for the stump 6a, 6b, and 6c comprise an axial seat 14 which is formed in the body 2 starting from its proximal end. Conveniently, the seat 14 is divided into two portions, starting from its inlet formed at the proximal end 5: a first portion 15 is prism-shaped, and a second portion 16 lies coaxially to the portion 15 and is threaded.

The stumps 6a, 6b, and 6c are provided with a protrusion 17 which is preferably prism-shaped, protrudes from their base, and is accommodated inside the first portion 15. The stumps 6a, 6b, and 6c are furthermore crossed, together with the protrusion 17, by an axial hole 18a, 18b, 18c which also passes through the protrusion 17 and is used to fix the stump to the body 2 by means of a screw 19 which can be inserted through the hole 18a, 18b, 18c and can be coupled to the second threaded portion 16 of the axial seat 14.

Inside the stump, the hole 18a, 18b, and 18c has a narrower portion that forms a shoulder 41 for the head 19a of the screw 19 that axially locks the stump on the body 2, whereas rotational locking is ensured by the side-fitting mutual engagement of the protrusion 17 and of the first portion 15 of the seat 14.

As shown in particular in FIG. 5, the stump 6a has a base 20 from which the protrusion 17 extends downward; the remaining part 21 of the stump 6a lies at an angle with respect to the axis of the base 20, which substantially coincides with the axis of the protrusion 17, so as to allow to reconstruct teeth with an orientation that is compatible with the orientation of the adjacent teeth, in a per se known manner. This orientation can also be changed by changing the rotational position of the stump with respect to the body 2, using the side-fitting coupling of the first portion 15 of the seat 14 with the protrusion 17.

As shown in FIG. 6 and in FIG. 7, the stump 6b, 6c can have a slightly tapered shape that is axially aligned with the protrusion 17, optionally with a frustum-like base 22 in which the smaller end face is directed towards the protrusion 17, as shown in particular for the stump 6b. A flat region 23 is formed on the lateral surface of the stumps 6b and 6c and is used as rotational reference for the position of the stump with respect to the body 2 during the various operations required to determine the exact orientation of the stump in the patient's mouth.

The prosthetic implant according to the invention also includes a plug screw, generally designated by the reference numeral 43, which has a threaded portion 24 that is to engage the second portion 16 of the seat 14 to close, with its head 25, the inlet of the seat 14 during the period in which the body 2 integrates with the bone.

There is also a healing screw 26, shown in FIG. 10, which also has a threaded portion 27 adapted to couple in the second portion 16 of the seat 14 and has a frustum-shaped head in which the smaller end face is directed towards the threaded portion 27 and has a diameter which substantially coincides with the diameter of the body 2 at its proximal end. The healing screw 26 is associated with the body 2 after its integration with the bone, while the false tooth or prosthesis is being prepared, so as to close the seat 14 and delimit the growth of the gingival tissue 28 during healing, limiting injury and bleeding in the subsequent application of the false tooth or prosthesis.

A prism-shaped seat 30 is formed both in the head of the plug screw 43 and in the head of the healing screw 26 in order to screw or unscrew both screws by means of an Allen-type tool.

The prosthetic implant according to the invention also includes a so-called transfer stump, shown in FIG. 8 and designated by the reference numeral 31, which has a substantially cylindrical body 32 that has, on its lateral surface, a flat region 33 which acts as reference for its rotational position. A prism-like protrusion 34 extends below the body 32 and is to be coupled to the first portion 15 of the seat 14 and to a substantially cylindrical protrusion 35 which is coaxial to said protrusion 34 and is to be accommodated inside the second portion 16 of the seat 14. Said transfer stump is used in a per se known manner, in forming the plaster model that duplicates the condition of the patient's mouth and is used during the construction of the false tooth or prosthesis.

Finally, there is a plaster bush 36 inside which a seat 37 is formed axially starting from one of its longitudinal ends. Said seat 37 is substantially formed like the seat 14 of the intrabony body 2, and the bush 36 is embedded in the plaster model used to construct the false tooth or the prosthesis to be applied.

In practice, the intrabony body 2 is inserted, in a per se known manner, in a receptacle 3 formed in the bone tissue at the missing tooth or at the point where a prosthesis is to be anchored, so that its proximal end 5 is arranged flush with the bone tissue. Once the period required to achieve adequate integration of the body 2 in the bone has passed, the tooth is constructed, or the prosthesis to be applied is prepared, on the stump 6a, 6b, 6c. The tooth or prosthesis is formed on a plaster model by using the bush 36 and the transfer stump 31 in a per se known manner.

During the forming of the false tooth or of the prosthesis, the healing screw 26 is mounted on the body 2 so as to allow the gingival mucous membrane 28 to heal so as to perfectly mate with the base of the false tooth or of the prosthesis fixing stump, avoiding the danger of injury to the gum.

It should be noted that when bone shrinkage occurs at the implant, the gingival mucous membrane 28 makes contact at the most with the portion 8 of the intrabony body 2, which causes no significant irritation of the gingival mucous membrane since it is smooth.

In practice it has been observed that the prosthetic implant according to the present invention fully achieves the intended aim and objects, since it ensures excellent bone integration and can significantly limit irritations of the gingival mucous membrane following bone shrinkage at the implant.

The prosthetic implant thus conceived is susceptible of numerous modifications and variations, all of which are within the scope of the inventive concept; all the details may furthermore be replaced with other technically equivalent elements.

In practice, the materials employed, so long as they are compatible with the specific use, as well as the dimensions, may be any according to the requirements and the state of the art.

What is claimed is:

1. A prosthetic implant for prosthodontics comprising:

an elongated intrabony body for substantially full insertion within a receptacle formed in a mandibular or maxillary bone, said intrabony body having a distal end and a proximal end adapted for being located at a surface layer of the mandibular or maxillary bone when said intrabony body is substantially fully inserted within the receptacle of the mandibular or maxillary bone, and said intrabony body having a longitudinal extension with a longitudinal axis extending between the distal and proximal ends;

wherein said intrabony body has at least one intermediate portion of the longitudinal extension arranged between said distal and proximal ends that has a prism shape and that has a rectilineal cross-section taken in a plane substantially perpendicular to the longitudinal axis of said intrabony body for preventing rotation of the intrabony body about the longitudinal axis when said intrabony body is fixed within the receptacle of the mandibular or maxillary bone; and wherein said intrabony body has a lower portion arranged between said distal end and said intermediate portion and an upper portion arranged between said proximal end and said intermediate portion, said upper and lower portions of said intrabony body having a substantially cylindrical shape; and wherein said intrabony body further has a pair of circumferential grooves in the outer surface of said intrabony body respectively arranged between the lower portion and the intermediate portion and the upper portion and the intermediate portion such that the circumferential grooves have a diameter which is less than the maximum diameters of the outer surfaces of the upper and lower portions and the intermediate portion for preventing axial displacement of the intrabony body when said intrabony body is fixed within the receptacle of the mandibular or maxillary bone.

2. The prosthetic implant of claim 1 wherein said intrabony body comprises two said intermediate portions, said pair of circumferential grooves being arranged at opposite ends of said two said intermediate portions, and said intrabony body further comprising a third circumferential groove arranged between said two said intermediate portions in the outer surface of said intrabony body such that the diameter of the third groove is less than the maximum diameters of the two said intermediate portions.

3. The prosthetic implant of claim 1 wherein said intrabony body is provided at said proximal end with an axial seat having a threaded portion for connecting a prosthesis supporting stump to said intrabony body.

4. The prosthetic implant of claim 1 wherein the external surface of said intrabony body has a roughness that is adapted to increase its integration in the bone except for a smooth portion which is provided starting from said proximal end.

5. Prosthetic implant for prosthodontics comprising:

an elongated intrabony body made of titanium for substantially full insertion within a receptacle formed in a mandibular or maxillary bone, said intrabony body having a distal end and a proximal end adapted for being located at a surface layer of the mandibular or maxillary bone when said intrabony body is substantially fully inserted within the receptacle of the mandibular or maxillary bone, and said intrabony body having a longitudinal extension with a longitudinal axis extending between the distal and proximal ends;

engagement means for connecting a stump that supports a false tooth or a prosthesis with said intrabony body adjacent said proximal end;

wherein the external surface of said intrabony body has a roughness that is adapted to increase its integration in the bone except for a smooth portion which is provided starting from said proximal end; and wherein said intrabony body has at least one intermediate portion of the longitudinal extension arranged between said distal and proximal ends that has a prism shape and that has a rectilineal cross-section taken in a plane substantially perpendicular to the longitudinal axis of said intrabony body for preventing rotation of the intrabony body about the longitudinal axis when said intrabony body is fixed within the receptacle of the mandibular or maxillary bone; and wherein said intrabony body has a lower portion arranged between said distal end and said intermediate portion and an upper portion arranged between said proximal end and said intermediate portion, said upper and lower portions of said intrabony body having a substantially cylindrical shape; and wherein said intrabony body further has a pair of circumferential grooves arranged in the outer surface of said intrabony body respectively arranged between the lower portion and the intermediate portion and the upper portion and the intermediate portion such that the circumferential grooves have a diameter which is less than the maximum diameters of the outer surfaces of the upper and lower portions and the intermediate portion for preventing axial displacement of the intrabony body when said intrabony body is fixed within the receptacle of the mandibular or maxillary bone.

6. Prosthetic implant according to claim 5, wherein said intrabony body comprises two said intermediate portions, said pair of circumferential grooves being arranged at opposite ends of said two said intermediate portions, and said intrabony body further comprising a third circumferential groove arranged between said two said intermediate portions in the outer surface of said intrabony body such that the diameter of the third groove is less than the maximum diameters of the two said intermediate portions.

7. Prosthetic implant according to claim 5, wherein said intrabony body is crossed by a transverse hole proximate to its distal end.

8. Prosthetic implant according to claim 7, wherein said intrabony body has, at said distal end, an axial hole that leads into said transverse hole.

9. Prosthetic implant according to claim 7, wherein said intrabony body has, on the outer surface of said intrabony proximate to said distal end, recesses which are angularly spaced from said transverse hole about the longitudinal axis of the intrabony body.

10. Prosthetic implant according to claim 5, wherein an axial seat is formed in said intrabony body starting from said proximal end and extending partially inside said intrabony body.

11. Prosthetic implant according to claim 10, wherein said seat includes, starting from said proximal end, a first prism-shaped portion and a second threaded portion, said first portion and said second portion being mutually coaxial.

12. Prosthetic implant for prosthodontics comprising:

an elongated intrabony body made of titanium for substantially full insertion within a receptacle formed in a mandibular or maxillary bone, said intrabony body having a distal end and a proximal end adapted for being located at a surface layer of the mandibular or maxillary bone when said intrabony body is substantially fully inserted within the receptacle of the mandibular or maxillary bone, and said intrabony body having a longitudinal extension with a longitudinal axis extending between the distal and proximal ends;

a stump supporting a false tooth or a prosthesis;

engagement means for connecting said stump with said intrabony body adjacent said proximal end;

wherein the external surface of said intrabony body has a roughness that is adapted to increase its integration in the bone except for a smooth portion which is provided starting from said proximal end; and wherein said intrabony body has at least one intermediate portion of the longitudinal extension arranged between said distal and proximal ends that has a prism shape and that has a rectilineal cross-section taken in a plane substantially perpendicular to the longitudinal axis of said intrabony body for preventing rotation of the intrabony body about the longitudinal axis when said intrabony body is fixed within the receptacle of the mandibular or maxillary bone; and wherein said intrabony body has a lower portion arranged between said distal end and said intermediate portion and an upper portion arranged between said proximal end and said intermediate portion, said upper and lower portions of said intrabony body having a substantially cylindrical shape; and wherein said intrabony body further has a pair of circumferential grooves in the outer surface of said intrabony body respectively arranged between the lower portion and the intermediate portion and the upper portion and the intermediate portion such that the circumferential grooves have a diameter which is less than the maximum diameters of the outer surfaces of the upper and lower portions and the intermediate .portion for preventing axial displacement of the intrabony body when said intrabony body is fixed within the receptacle of the mandibular or maxillary bone; and wherein an axial seat is formed in said intrabony body starting from said proximal end and extending partially inside said intrabony body, and wherein said seat includes, starting from said proximal end, a first prism-shaped portion and a second threaded portion, said first portion and said second portion being mutually coaxial; and wherein said stump has an elongated shape with a base that is directed towards said intrabony body when said stump is connected with said intrabony body and is provided with a prism-shaped protrusion for coupling to said first portion of said seat and is crossed by an axial hole, said engagement means comprising a screw for insertion through said axial hole of said stump and for engaging said second portion of said seat to fix said stump to said intrabony body.

13. Prosthetic implant according to claim 12, wherein the base of said stump is substantially frustum-shaped and tapers towards said protrusion.

14. Prosthetic implant according to claim 12, wherein an upper remaining part of said stump extends at an angle with respect to said base.

15. Prosthetic implant according to claim 12, wherein an upper remaining part of said stump is substantially frustum-shaped and extends coaxially to said base.

16. Prosthetic implant according to claim 12, wherein said stump has, on the lateral surface of the stump, a flat portion for rotational reference.

17. Prosthetic implant according to claim 12, further comprising a healing screw which is adapted to close said seat of said intrabony body, said healing screw having a threaded stem for insertion in said second portion of the seat of said intrabony body, and a frustum-shaped head with a smaller end face of said head being directed towards said threaded stem and having a diameter that is substantially equal to the diameter of said intrabony body at said proximal end.

\* \* \* \* \*